(12) United States Patent
Lee et al.

(10) Patent No.: US 7,232,617 B2
(45) Date of Patent: Jun. 19, 2007

(54) ELECTROLUMINESCENT DEVICES

(75) Inventors: Shuit-Tong Lee, Hong Kong (CN);
Chun-Sing Lee, Hong Kong (CN);
Peng-Fei Wang, Hong Kong (CN);
Bao-Xiu Mi, Hong Kong (CN)

(73) Assignee: Cityu Research Limited, Kowloon, Hong Kong (CN)

( * ) Notice: Subject to any disclaimer, the term of this patent is extended or adjusted under 35 U.S.C. 154(b) by 0 days.

(21) Appl. No.: 10/357,616

(22) Filed: Feb. 4, 2003

(65) Prior Publication Data

US 2004/0151943 A1  Aug. 5, 2004

(51) Int. Cl.
*H01J 1/62* (2006.01)
*C07D 209/744* (2006.01)

(52) U.S. Cl. .................. 428/690; 428/917; 313/504; 313/506; 252/301.16; 257/E51.048

(58) Field of Classification Search ............... 428/690, 428/917; 429/917; 313/504, 506, 507, 503; 257/40, E51.048; 252/301.16; 548/470, 548/472
See application file for complete search history.

(56) References Cited

U.S. PATENT DOCUMENTS

| | | | | |
|---|---|---|---|---|
| 3,172,862 A | | 3/1965 | Gurnee et al. ........... 252/301.3 |
| 3,173,050 A | | 3/1965 | Gurnee et al. ............. 313/108 |
| 3,403,296 A | * | 9/1968 | Zweig ........................ 315/246 |
| 4,539,507 A | | 9/1985 | VanSlyke et al. ........... 313/504 |
| 4,769,292 A | * | 9/1988 | Tang et al. .................. 428/690 |
| 4,885,211 A | | 12/1989 | Tang et al. .................. 428/690 |
| 5,059,862 A | | 10/1991 | VanSlyke et al. ........... 313/503 |
| 5,069,975 A | | 12/1991 | Nakada et al. ............. 428/457 |
| 5,104,740 A | | 4/1992 | Shinkai et al. ............. 428/457 |
| 5,126,214 A | | 6/1992 | Tokailin et al. ............. 428/690 |
| 5,141,671 A | | 8/1992 | Bryan et al. ........... 252/301.16 |
| 5,281,489 A | * | 1/1994 | Mori et al. .................. 428/690 |
| 5,389,444 A | | 2/1995 | Hosokawa et al. ......... 428/457 |
| 5,409,783 A | * | 4/1995 | Tang et al. .................. 428/690 |
| 5,593,788 A | | 1/1997 | Shi et al. ..................... 428/690 |
| 5,935,720 A | | 8/1999 | Chen et al. ................. 428/690 |
| 5,972,247 A | | 10/1999 | Shi et al. ..................... 252/583 |
| 6,020,078 A | | 2/2000 | Chen et al. ................. 428/690 |
| 6,165,383 A | | 12/2000 | Chou ..................... 252/301.16 |
| 6,242,115 B1 | | 6/2001 | Thomson et al. ........... 428/690 |
| 6,245,449 B1 | | 6/2001 | Tamano et al. ............. 428/690 |
| 6,333,521 B1 | | 12/2001 | Thompson et al. ........... 257/79 |
| 6,630,253 B1 | * | 10/2003 | Tanaka et al. ............... 428/690 |
| 6,670,053 B2 | * | 12/2003 | Conley ........................ 428/690 |
| 6,693,295 B2 | * | 2/2004 | Nii ................................ 257/40 |

FOREIGN PATENT DOCUMENTS

| EP | 0699654 | | 3/1999 | .................. 211/54 |
|---|---|---|---|---|
| JP | 2000-228286 | * | 8/2000 | |
| JP | 2002-289351 | * | 10/2002 | |

OTHER PUBLICATIONS

Ding et al., "Synthesis of Highly Fluorescent Materials: Isoindole-Containing Polymers", Journal of Polymer Science: Part A: Polymer Chemistry, vol. 37, pp. 3293-3299 (1999).*
Gauvin et al., "Organic light emitting devices containing a highly substituted isoindole or polyisoindole", Thin Solid Films, vol. 353, Issues 1-2, Sep. 29, 1999, pp. 218-222.*
J.L Segura, "The Chemisty of Electroluminescent Organic Materials," *Acta Polym.* 49, 319-44 (1998).
C.W. Tang and S.A. Van Slyke, "Organic Electroluminescent Diodes," *Appl. Phys. Lett.*, 51 (12), 913-15 (1987).
C.H. Chen et al., "Recent Developments in Molecular Organic Electroluminescent Materials," *Macromol. Symp.* 125, 1-48 (1997).
U.Mitschke and P. Bäuerle, "The Electroluminescence of Organic Materials," *J. Mater. Chem.* 10, 1471-1507 (2000).
Y. Shirota, "Organic Materials for Electronic and Optoelectronic Devices," *J. Mater. Chem.* 10, 1-25 (2000).
U.S. Appl. No. 10/229,493, filed Aug. 28, 2002, "Electroluminescence Devices Using Pyrazolo [3,4b] Quinoxaline Derivatives."

* cited by examiner

*Primary Examiner*—Rena Dye
*Assistant Examiner*—Camie S. Thompson
(74) *Attorney, Agent, or Firm*—Heslin Rothenberg Farley & Mesiti P.C.

(57) ABSTRACT

A compound of formula [I]:

X—R  [I]

wherein X represents the group:

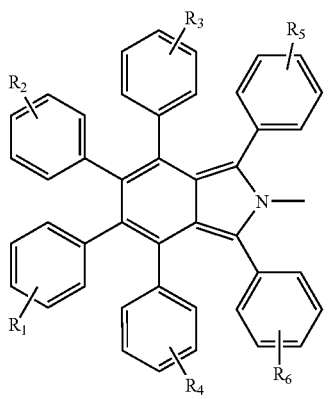

and R is either (i) represented by the formula [II]

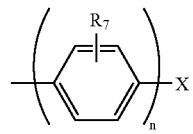

[II]

wherein n is 1 or 2, and the or each $R_7$ group is independently selected from the group consisting of hydrogen and halogen atoms, cyano, nitro, mercapto, carbonyl and sulfone groups, and optionally substituted alkyl, haloalkyl, hydroxyalkyl, aryl, alkoxy, aryloxy, alkylamino, arylamino, alkylthio, arylthio, ester, siloxy, cyclic hydrocarbon and heterocyclic groups;

or (ii) is selected from the group consisting of optionally substituted alkyl, hydroxyalkyl, aryl, cyclic hydrocarbon and heterocyclic groups;

wherein in each case $R_1$–$R_6$ are each independently selected from the group consisting of hydrogen and halogen atoms, cyano, nitro, mercapto, carbonyl and sulfone groups, and optionally substituted alkyl, haloalkyl, hydroxyalkyl, aryl, alkoxy, aryloxy, alkylamino, arylamino, alkylthio, arylthio, ester, siloxy, cyclic hydrocarbon and heterocyclic groups. The compounds are useful as hole-transporting materials in electroluminescence devices.

23 Claims, 4 Drawing Sheets

ELECTROLUMINESCENT DEVICES

FIELD OF THE INVENTION

This invention relates to organic electroluminescence (EL) devices and, more particularly, to the use of novel highly phenylated isoindole derivatives for thin-film type organic electroluminescence devices with good thermal and chemical stabilities.

BACKGROUND TO THE INVENTION

In the 1960s, many trials for the preparation of an organic electroluminescence device were reported using conjugated materials generally having fused aromatic rings (U.S. Pat. No. 3,172,862, issued 1965; U.S. Pat. No. 3,173,050, issued 1965). The efficiencies and lifetimes of these organic EL devices were much lower than those obtained from inorganic systems at the same time, so research mainly focused on the inorganic materials. The reason for the low luminance of the early organic EL devices is the highly resistive EL medium, which prevents the efficient injection of carriers into the light-emitting layer. Tang and VanSlyke solved this problem successfully in the late 1980s (Tang and VanSlyke, Appl. Phys. Lett. 1987, 51, 913). They improved the performance of an organic EL device significantly by using a structure with two thin layers: a hole-transporting layer of an organic substance laminated on an organic emitting layer. This work revived the research on organic EL devices, and resulted in the development of a new generation of light-emitting diodes with organic dyes. Since then, much work has been done to further improve the efficiency, stability, colour purity and so forth of such devices (U.S. Pat. Nos. 5,141,671; 4,539,507; 6,020,078; 5,935,720; 5,972,247; 5,593,788; 4,885,211; 5,059,862; 5,104,740; 5,069,975; 5,126,214; 5,389,444; 6,165,383; 6,245,449; Chen, Shi and Tang, Macromol. Symp., 1997, 125, 1; Segura, Acta. Polym., 1998, 49, 319; Mitschke and Bauerle, J. Mater. Chem. 2000, 10, 1471).

Performance stability of EL devices is a very important consideration for practical applications. A number of factors are known to influence the device stability. These include thermal and chemical stability of materials (including hole-transporting materials, electron-transporting materials and emitting materials, etc.), carrier mobility of electron and hole-transporting materials, the configuration of device, as well as environmental factors. To address these problems, several useful methods have been developed and are well documented. For example, one is to dope a strongly emitting material into a host material to form a guest-host system. It has been shown that an organic EL device with good efficiency and high stability, as well as desired colour with proper chromaticity, can be obtained by doping different strongly emitting materials into a host material such as tri-(8-hydroxyquinolinato)aluminum ($AlQ_3$).

The thermally induced deformation of the hole-transporting materials is thought to be one of the main causes of degradation. Thus, many studies have been focused on the design and preparation on new hole-transporting materials, and the relationship between the properties (e.g. Tg) and molecular structure (U.S. Pats. No. 6,242,115; 6,333,521; EP 0,699,654 A1; Shirota, J. Mater. Chem., 2000, 10, 1). Isoindole derivatives have been synthesized by the reaction of phthalaldehyde and an amine in the presence of an alkylthiol which was used as the detection method for amino acids, peptides, and proteins. It has also been found that isoindole derivatives are highly fluorescent emitting in blue. Some highly fluorescent polymers containing isoindole moiety have been prepared and showed properties of high glass transition temperatures and high thermal stabilities. However, these materials have never been used in small molecule organic EL devices.

The object of the present invention is to provide novel compounds which are suitable for use as hole-transporting materials in organic electroluminescence devices. These compounds should be highly thermally stable, and should have a similar hole-transporting ability to known hole-transporting compounds.

SUMMARY OF THE INVENTION

The present invention provides a compound of formula [I]:

$$X\text{---}R \qquad [I]$$

wherein X represents the group:

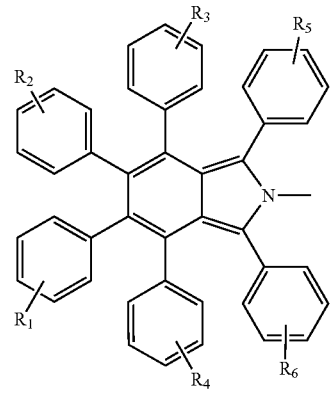

and R is either (i) represented by the formula [II]

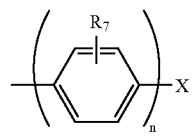

wherein n is 1 or 2, and the or each $R_7$ group is independently selected from the group consisting of hydrogen and halogen atoms, cyano, nitro, mercapto, carbonyl and sulfone groups, and optionally substituted alkyl, haloalkyl, hydroxyalkyl, aryl, alkoxy, aryloxy, alkylamino, arylamino, alkylthio, arylthio, ester, siloxy, cyclic hydrocarbon and heterocyclic groups;

or (ii) is selected from the group consisting of optionally substituted alkyl, hydroxyalkyl, aryl, cyclic hydrocarbon and heterocyclic groups;

wherein in each case $R_1$–$R_6$ are each independently selected from the group consisting of hydrogen and halogen atoms, cyano, nitro, mercapto, carbonyl and sulfone groups, and optionally substituted alkyl, haloalkyl, hydroxyalkyl, aryl, alkoxy, aryloxy, alkylamino, arylamino, alkylthio, arylthio, ester, siloxy, cyclic hydrocarbon and heterocyclic groups.

The invention also provides an organic electroluminescence device comprising:

an anode;

a cathode;

a hole-transporting layer; and an electron-transporting layer wherein the hole-transporting layer is disposed between the anode and the electron-transporting layer and the electron-transporting layer is disposed between the cathode and the hole-transporting layer, and the hole-transporting layer comprises a compound of formula [I]:

X—R [I]

wherein X represents the group:

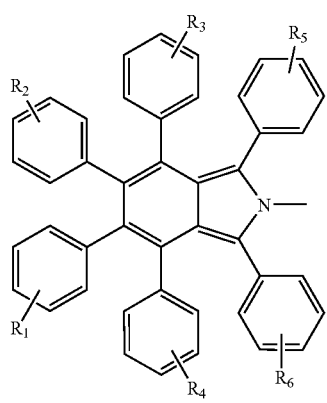

and R is either (i) represented by the formula [II]

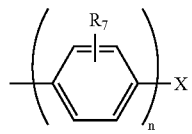

[II]

wherein n is 1 or 2, and the or each $R_7$ group is independently selected from the group consisting of hydrogen and halogen atoms, cyano, nitro, mercapto, carbonyl and sulfone groups, and optionally substituted alkyl, haloalkyl, hydroxyalkyl, aryl, alkoxy, aryloxy, alkylamino, arylamino, alkylthio, arylthio, ester, siloxy, cyclic hydrocarbon and heterocyclic groups;

or (ii) is selected from the group consisting of optionally substituted alkyl, hydroxyalkyl, aryl, cyclic hydrocarbon and heterocyclic groups;

wherein in each case $R_1$–$R_6$ are each independently selected from the group consisting of hydrogen and halogen atoms, cyano, nitro, mercapto, carbonyl and sulfone groups, and optionally substituted alkyl, haloalkyl, hydroxyalkyl, aryl, alkoxy, aryloxy, alkylamino, arylamino, alkylthio, arylthio, ester, siloxy, cyclic hydrocarbon and heterocyclic groups.

The invention further provides the use of a compound of formula [I], as described above, as a hole-transporting material in an electroluminescence device. There is also provided a method of using a compound of formula [I] in an electroluminescence device, the method comprising providing a compound of formula [I], and incorporating said compound as a hole-transporting material within an electroluminescence device which also comprises an anode, a cathode and an electron-transporting material.

The isoindole derivatives of compound [I] which are described in the present invention are highly bulky compounds and contain an electron rich $sp^3$ nitrogen atom. The combination of these properties results in good hole-transporting ability, high thermal stability, as well as good film-forming properties. Moreover, the compounds disclosed here are also highly fluorescent. The compounds have similar performance to N,N'-bis-(1-naphthyl)-N,N'-diphenyl-1,1'-biphenyl-4,4'-diamine. Thus, it is desirable to use these isoindole derivatives as hole-transporting materials to make organic electroluminescence devices with high thermal stable and improved efficiency.

DETAILED DESCRIPTION OF THE INVENTION

Figure 1:
FIGS. 1 and 2 show organic electroluminescence devices according to the present invention.

Unless otherwise stated in the following description, the term alkyl represents an alkyl group containing from 1 to 18, preferably 1 to 10, and more preferably 1 to 6, carbon atoms. Particularly preferred alkyl groups include methyl, ethyl, propyl, butyl, sec-butyl, tert-butyl, pentyl, hexyl, heptyl, octyl and stearyl.

The term halogen represents a chlorine, fluorine, bromine or iodine atom, with chlorine and fluorine being preferred. A group containing a halogen atom, e.g. haloalkyl, may contain one or more of these halogen atoms. Haloalkyl represents any alkyl group substituted by one or more halogen atoms. Preferably haloalkyl represents trichloromethyl or trifluoromethyl.

Hydroxyalkyl represents an alkyl group substituted with at least one hydroxy group. The alkyl group preferably has from 1 to 4 carbon atoms.

Aryl represents a cyclic hydrocarbon having at least one aromatic ring, and having from 5 to 30, preferably from 6 to 14, carbon atoms. Aryl preferably represents a group selected from the group consisting of phenyl, biphenyl, triphenyl, tetraphenyl, o-tolyl, m-tolyl, p-tolyl, o-xylyl, m-xylyl, p-xylyl, or o-cumenyl, m-cumenyl, p-cumenyl and styryl.

The terms alkenyl and alkynyl represent alkenyl and alkynyl groups respectively having from 2 to 18, preferably from 2 to 10, and more preferably from 2 to 6 carbon atoms.

The term alkoxy (or alkyloxy) represents an alkyl group linked via an oxygen atom. Preferably alkoxy represents methoxy, ethoxy, propoxy, butoxy, sec-butoxy, tert-butoxy or stearyloxy. Similarly, the terms alkenyloxy and aryloxy represent alkenyl and aryl groups respectively linked via an oxygen atom. Preferably aryloxy represents phenoxy.

Alkylamino represents any amino group of formula —NH$_2$, —NHR' or —NRR' where R and R' are alkyl groups, preferably having from 1 to 10, more preferably from 1 to 4, carbon atoms. Preferred amino groups are —NH$_2$, methyl amino (i.e.—NHMe), ethyl amino, propyl amino, butyl amino, sec-butyl amino, tert-butyl amino, pentyl amino, hexyl amino, heptyl amino, octyl amino, stearyl amino, dimethyl amino (i.e.—NMe$_2$), diethyl amino, dipropyl amino, dibutyl amino, disec-butyl amino, ditert-butyl amino, dipentyl amino, dihexyl amino, diheptyl amino, dioctyl amino and distearyl amino.

Arylamino represents any amino group of formula —NHR" or —NHR"R''' where R is an aryl group as defined above. The aryl group is preferably selected from the group consisting of phenyl, naphthyl, anthryl and tolyl. Preferred arylamino groups include phenylamino, diphenylamino, phenylnaphthylamino, phenylanthrylamino, o-tolylnaphthylamino, p-tolylnaphthylamino, m-tolyinaphthylamino, o-tolylanthrylamino, p-tolylanthrylamino, m-tolylanthrylamino and naphthylanthrylamino.

Alkylthio represents an alkyl group linked by a sulphur atom. Preferred alkylthio groups include methylthio, ethylthio, propylthio, butylthio, sec-butylthio and tert-butylthio. Similarly, arylthio represents an aryl group linked by a sulphur atom. Preferably arylthio represents phenylthio.

The term ester represents a group of formula —C(O)OR where R is a hydrogen atom or an alkyl group. Preferably the alkyl group has from 1 to 6, more preferably from 1 to 4, carbon atoms. The term carbonyl represents a group having the general formula —C(O)R, where R is a hydrogen atom or an alkyl group. The alkyl group preferably has from 1 to 6, more preferably 1 to 4, carbon atoms.

Siloxy represents a group of general formula —OSiR$_3$, where each R group is independently selected from the group consisting of a hydrogen atom and an alkyl group. The alkyl group preferably has from 1 to 6, more preferably 1 to 4, carbon atoms.

Cyclic hydrocarbon represents both mono- and polycyclic hydrocarbons, which may be saturated or unsaturated, having from 3 to 20, more preferably from 3 to 10, carbon atoms. Preferred cyclic hydrocarbons include mesityl, pentarhenyl, indenyl, naphthyl, azulenyl, heptalenyl, acenaphtylenyl, phenalenyl, fluorenyl, anthryl, anthraquinonil, phenantolyl, pyrenyl, crysenyl, picenyl, rebicenyl and trinaphthylenyl The term heterocyclic represents groups having between 3 and 20, more preferably between 3 and 10, carbon atoms and having one or more 4, 5, 6 or 7 member saturated or unsaturated rings containing 1, 2 or 3 oxygen, nitrogen or sulphur atoms. Preferred heterocyclic groups include pyranthrenyl, oparenyl, thienyl, furyl, pyrrolyl, imidazolyl, pyrazolyl, pyridyl, pylazinyl, pyrimidinyl, pyridazinyl, indolyl, quinolyl, isoquinolyl, phthalazinyl, quinoxalynyl, quinazolynyl, carbazolyl, acrydinyl, phenadinyl, furluryl, isochiazolyl, isothiazolyl, isoquixazolyl, furazanyl, phenoquisadinyl, benzthiazolyl, benzoxazlyl and benzoimidazolyl.

Mercapto represents the group —SH.

Sulfone represents a group having the general formula —SO$_2$R, where R is a hydrogen atom or an alkyl group. The alkyl group preferably has from 1 to 6, more preferably 1 to 4, carbon atoms.

When any of the groups listed above are described as optionally substituted, the substituent groups include halogen atoms, hydroxy, cyano, amino, nitro, alkyl, cyclic hydrocarbon, haloalkyl, alkoxy, haloalkoxy, carboxyl, alkylthio, alkylamino, arylamino, ester, siloxy, aryl, aryloxy, alkenyl, alkenyloxy and alkynyl, as well as cyclic hydrocarbon and heterocyclic groups. Preferred optional substituents include alkyl, haloalkyl, aryl, alkoxy, aryloxy, alkylamino, arylamino, alkylthio, arylthio, ester, siloxy, cyclic hydrocarbon and heterocyclic groups, with alkyl groups being particularly preferred.

The compounds of the invention are represented by the general formula [I], as shown above. In one embodiment, it is preferred that the compound has the general formula [III]:

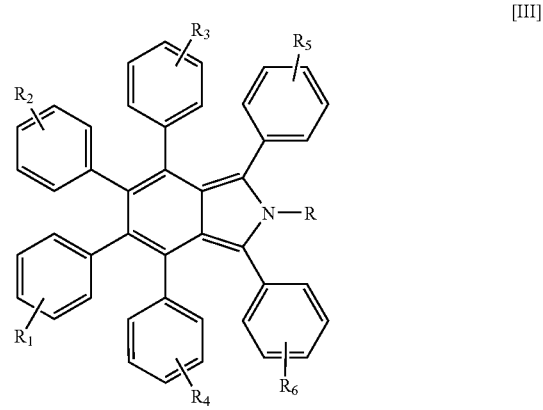

[III]

wherein the R$_1$–R$_6$ groups are as defined above. In this embodiment, it is preferred that R is selected from the group consisting of alkyl, haloalkyl, aryl and heterocyclic groups.

In another embodiment, it is preferred that the compound of general formula [I] has the formula [IV]:

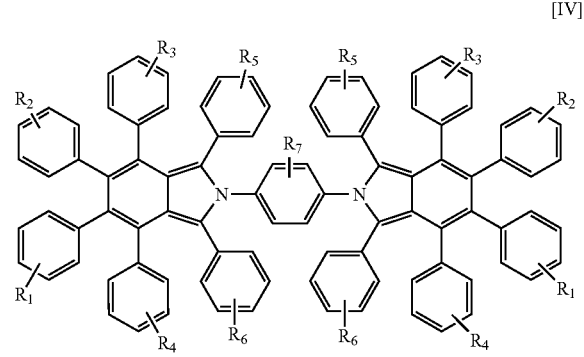

[IV]

wherein R$_1$–R$_6$ are as defined earlier. In this embodiment, it is preferred that the or each R$_7$ group is independently selected from the group consisting of alkyl, haloalkyl, aryl and heterocyclic groups.

In a further embodiment, it is preferred that the compound of general formula [I] has the formula [V]:

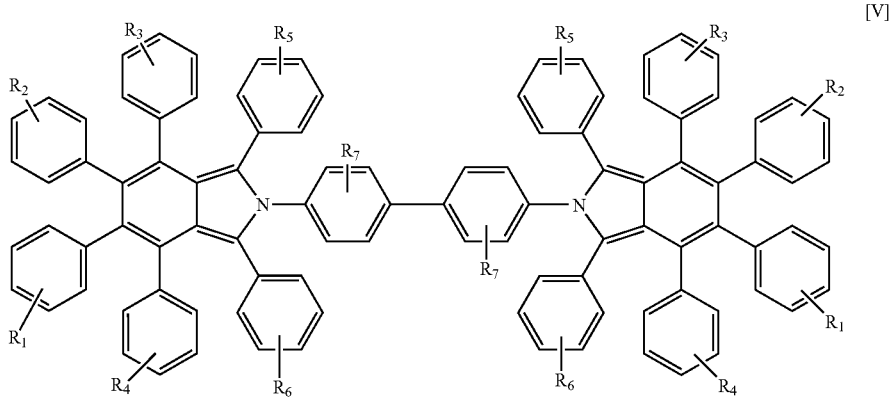

[V]

wherein $R_1$–$R_6$ are as defined earlier. It is preferred that the or each $R_7$ group is independently selected from the group consisting of alkyl, haloalkyl, aryl and heterocyclic groups.

In each of the three embodiments given above, it is preferred that the groups $R_1$–$R_6$ are selected from the group consisting of alkyl, haloalkyl, aryl and heterocyclic groups. It is particularly preferred that each of $R_1$–$R_6$ are hydrogen atoms.

In the case of formulae [IV] and [V] described above, it is not necessary that corresponding R groups on opposite sides of the molecule are the same, that is, it is not necessary that $R_1$ on the right-hand side of the molecule represents the same group as $R_1$ on the left-hand side of the molecule. However, symmetric molecules (i.e. where corresponding R groups on each side of the molecule are the same) may be easier to synthesise.

As stated above, the invention also provides an organic electroluminescence device having a hole-transporting layer comprising a compound of formula [I]. Preferred compounds of the general formula [I] have already been discussed.

The electroluminescence devices of the invention have a conventional general structure, comprising an anode, a cathode, a hole-transporting layer and an electron transporting layer. The devices can be mounted on a substrate, with the substrate being in contact with either the anode or the cathode. The devices are capable of emitting light, and hence contain a luminescent material, which may be present as a component in the hole-transporting layer or in the electron transporting layer, or may be present as a separate luminescent, or light-emitting, layer.

Figure 2:
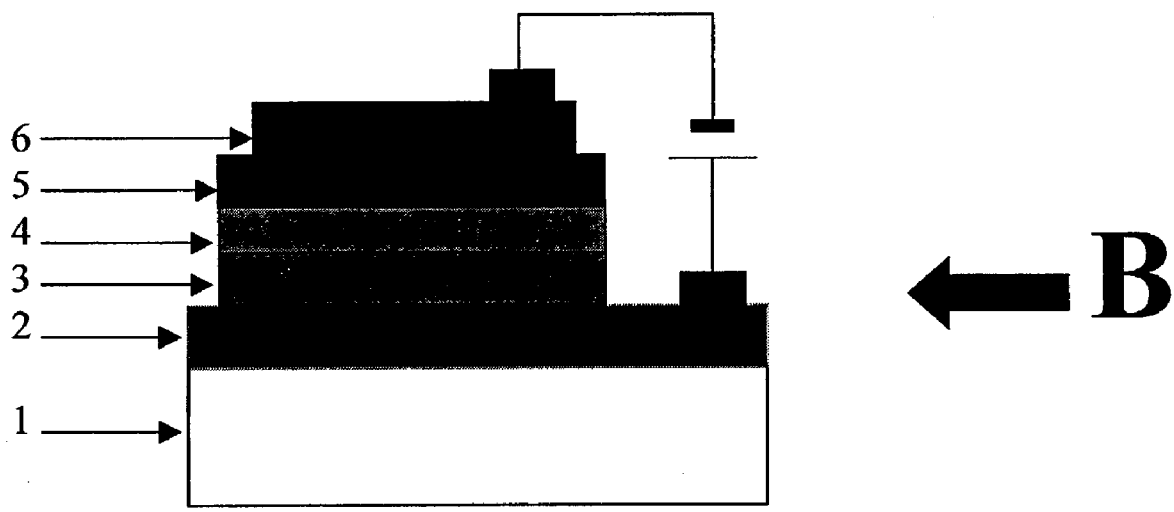

The components of the electroluminescence devices of the present invention will now be described individually in more detail. Representative examples are depicted in FIGS. 1 and 2, which illustrate organic electroluminescence device structures A and B according to the invention. Reference numeral 1 indicates a substrate, numeral 2 indicates an anode, numeral 3 indicates an organic hole-transporting layer, numeral 4 indicates an organic light-emitting (or luminescent) layer, numeral 5 indicates an organic electron-transporting layer, and numeral 6 indicates a cathode.

Substrate

The substrate is used as a support for the organic electroluminescence device of the present invention. It preferably consists of a quartz or glass sheet, a metal sheet or foil, or a plastic film or sheet. However, the most preferred materials are glass sheet or transparent synthetic resin such as polyester, polycarbonate, and polysulfone. The substrate can be in contact with the anode, or alternatively can be in contact with the cathode.

Anode and Cathode

The anode may comprise any suitable material known in the art, and usually comprises a metal such as silver, gold, aluminum, nickel or palladium; a metal oxide such as an oxide of indium and/or tin; carbon black or a conductive resin such as poly(3-methylthiophene).

The materials mentioned above for making the anode may also be employed for preparation of the cathode. However, the preferred material for the cathode is a metal having a low work function, which is favourable to the efficient injection of electrons. Thus, a suitable metal such as magnesium, aluminum, silver and indium, or alternatively their alloys may be used.

The method for preparing the anode and the cathode may be any conventional technique known in the art, but is preferably vacuum deposition or sputtering. However, when the material is in the form of fine particles of a metal, carbon black, a metal oxide or a conductive resin powder, it can be dispersed into a suitable binder resin in solution and coated onto a substrate to form the electrodes. Furthermore, in the case of a conductive resin, a thin film may be formed directly on a substrate by electrolytic polymerization.

The anode or cathode can be made to have a multi-layered structure by depositing layers of the different materials mentioned above. However, preferably at least one of the electrodes has a transmittance of visible light of at least 60%, more preferably at least 80%. In this respect, this layer should not be too thick, generally from 5 to 1,000 nm, more preferably from 10 to 500 nm.

Electron-transporting Layer

The electron-transporting layer comprises an electron-transporting material which is such that electrons can be injected from the cathode easily; the mobility of transporting electrons is excellent; and the migration of excitons generated in the light-emitting layer into hole injection zone is blocked. Moreover, a good capability of forming a thin film is also desirable.

Such an electron transport material generally has a large electron affinity, for example, thiopyrandioxide derivatives, perylene tetracarboxylic acid derivatives, oxadiazole derivatives, metal complexes of 8-hydroxyquinoline, 10-hydroxybenzo[h]quinoline, pyrrolopyridine derivatives and naphthylidine derivatives. Examples are shown as follows:

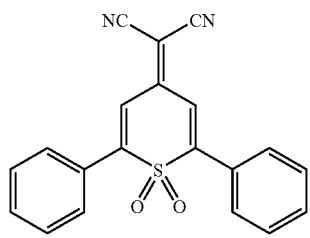

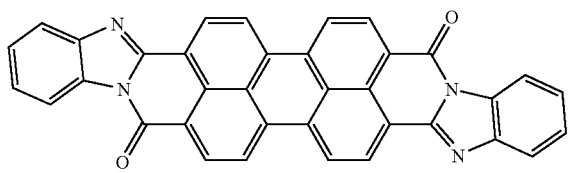

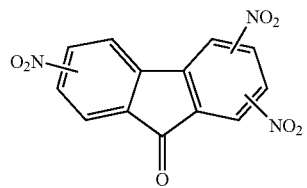

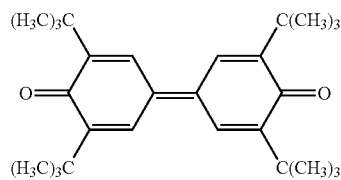

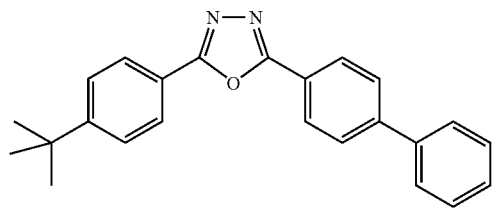

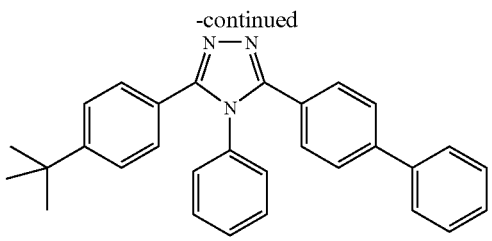

The electron-transporting layer can be formed by any conventional method, but is preferably formed by vacuum deposition or a coating/casting method. This electron-transporting layer usually has a thickness of from 5 to 400 nm, preferably from 30 to 100 nm. In order to obtain a uniformly thin film, the vacuum deposition method is preferred.

Luminescent Material

Electrons and holes recombine in the region of the luminescent material to produce excitons, which may decay to the ground state in a radiative way, resulting in an emission as either fluorescence or phosphorescence. This material is generally required to have a high emission quantum yield, a suitable energy gap, as well as a good ability to form uniformly thin films.

The luminescent or light-emitting material may be present as a separate light-emitting layer in the electroluminescent devices of the invention. Alternatively, the hole-transporting layer, or the electron-transporting layer, or both, may themselves act as the luminescent material. In this case, there is no limit on the nature of the hole-transporting layer or the electron-transporting layer, other than it must have the capacity to emit light.

Materials which are suitable for use as a luminescent material, either as a separate luminescent layer, or as a material incorporated within the hole-transporting layer or the electron-transporting layer, include fused aromatic compounds, such as naththrene, phenanthrene, anthracene, pyrene, tetracene, pentacene, coronene, chrysene, perylene, rubrene, phthaloperylene, derivatives of these, coumarin derivatives, benzidine type triphenylamine, styrylamine type triphenylamine, diamine type triphenylamine, thiopyrane derivatives, polymethine derivatives, 8-hydroxyquinolinato metal complexes, pyran derivatives, porphyrin derivatives, europium complexes, iridium complexes, salan-transition metal complexes, or other fluorescent or phosphorescent dyes.

Hole Transporting Layer

An organic hole-transporting layer is located on an anode. It generally consists of a compound that is able to transport holes efficiently from the anode to the organic emitting layer between the electrodes to which an electric field is applied. Therefore, such a compound should allow highly efficient hole injecting from the anode. It must also be capable of efficiently transporting the injected holes to an emitting layer or an emitting material, and is preferably capable of forming a uniformly thin film. Thus, in this respect, a suitable hole-transporting compound should usually have a low ionization potential, high hole mobility and stability. Moreover, the impurities likely to form traps should not be produced during preparation or use.

The compounds of formula [I] of the present invention, described above, are used in the hole-transporting layer of the present invention.

Hole-transporting materials which are preferably used in the organic electroluminescence device of the present invention include the compounds with formulas [III] [IV], [V]:

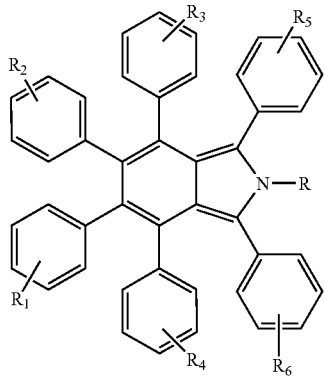

III

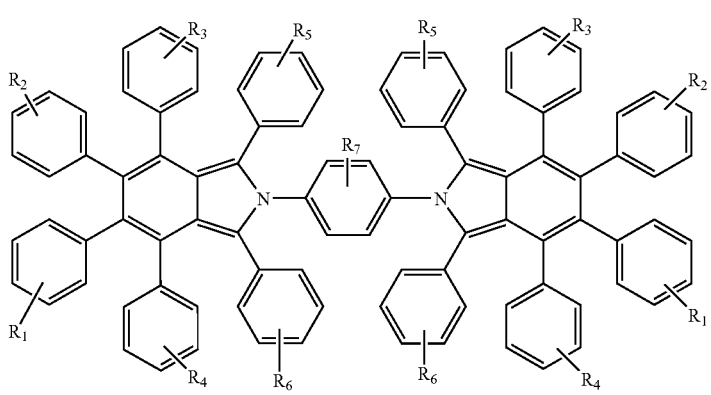

IV

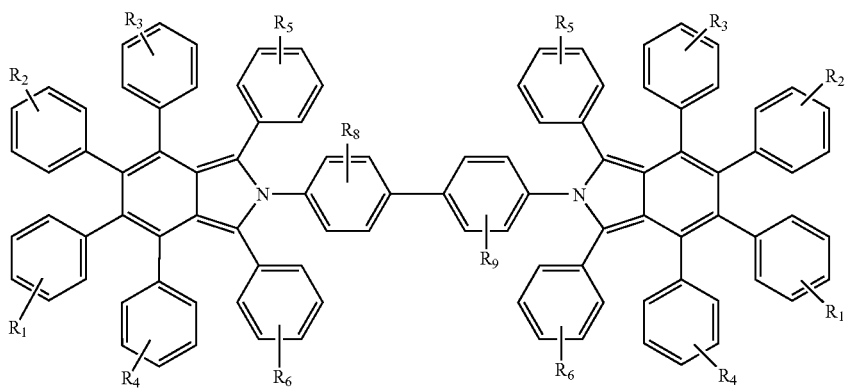

V wherein R is alkyl with 1–18 carbon atoms such as methyl, ethyl, propyl, butyl, sec-butyl, tert-butyl, pentyl, hexyl, heptyl, octyl, stearyl, hydroxyalkyl with 1–4 carbon atoms, styryl, phenyl, biphenylel, triphenylel, teraphenylel, o, m-, p-tolyl, xylyl, o-, m-, p-cumenyl, substituted or unsubstituted monocyclic hydrocarbon such as mesityl, pentarhenyl, indenyl, naphthyl, azulenyl, heptalenyl, acenaphtylenyl, phenalenyl, fluorenyl, anthraquinonil, phenantolyl, crysenyl, picenyl, rebicenyl, trinaphthylenyl, substituted or unsubstituted condensed polycyclic hydrocarbon such as oparenyl, thienyl, furyl, pyrrolyl, imidazolyl, pyrazolyl, pyridyl, pylazinyl, pyrimidinyl, pyridazinyl, indolyl, quinolyl, isoquinolyl, phthalazinyl, quinoxalynyl, quinazolynyl, carbazolyl, acrydinyl, phenadinyl, furluryl, isochiazolyl, isothiazolyl, isoquixazolyl, furazanyl, phenoquisadinyl, benzoxazlyl, independently, and $R_1$–$R_9$ are selected independently from the groups consisting of hydrogen, halogen, cyano, nitro, carbonyl, sulfone, ester, alkoxy, mercapto, alkyl with 1–18 carbon atoms, dialkylamino with 1–18 carbon atoms, diarylamino, stearyl, trichloromethyl, trifluoromethyl, hydroxyalkyl with 1–4 carbon atoms, styryl, alkoxyl, alkyloxy, alkylthio, aryloxy, arylthio, siloxy, aryl or substituted aryl, substituted or unsubstituted monocyclic hydrocarbon, substituted or unsubstituted condensed polycyclic hydrocarbon, substituted or unsubstituted heterocyclic hydrocarbon.

In addition to the compounds of the invention, additional hole-transporting materials may also be used. These additional hole-transporting materials include those disclosed in U.S. Pat. No. 5,935,720, thiophene derivatives, aromatic tertiary amines, phthalocyanine derivatives, naphthalocyanine derivatives, porphyrin derivatives, pyrazoline derivatives, carbazole derivatives, triphenylamine derivatives described by Y. Shirota in *J Mater. Chem*, 10, 1–25 (2000) and C. H. Chen, J. Shi, C. W. Tang in *Macromol. Symp*. 125, 1–48 (1997), and polymer materials such as polyvinylcarbazole and polysilane, although other suitable materials will be contemplated by the person skilled in the art. Particularly useful hole-transporting materials are illustrated as follows:

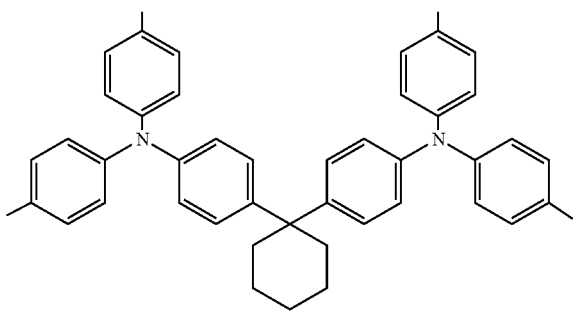

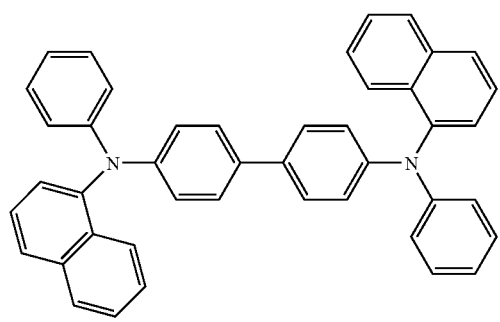

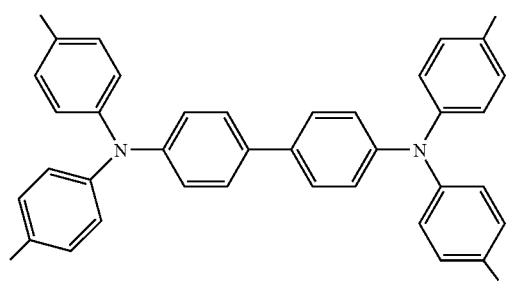

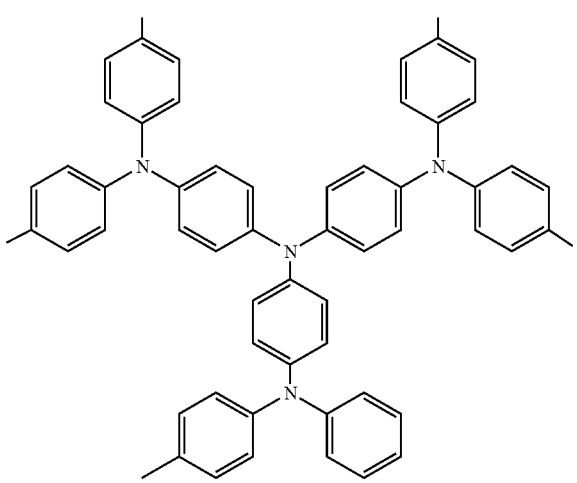

-continued

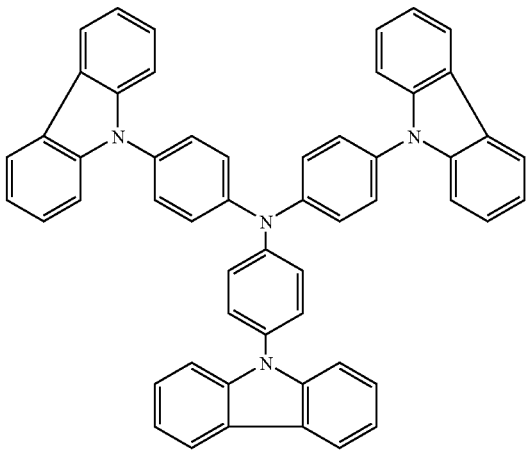

The materials mentioned above can be laminated onto the anode by any suitable method, although it is preferred to use a vacuum deposition method or a coating/casting method to form the hole-transporting layer of the present invention. This hole-transporting layer usually has a thickness of from 5–400 nm, preferably from 30–100 nm. In order to obtain a uniformly thin film, the vacuum deposition method is preferred.

Other Materials

Other variations and modifications of the devices described above will be apparent to the skilled person, however one particularly preferable embodiment includes a hole injection material disposed between the anode and the hole-transporting layer. This hole injection material enhances hole injection from the anode in the electroluminescence device, and is preferably present in the form of a thin layer. A suitable thickness is about 15 nm. Particularly useful materials include copper phthalocyanine, and the porphyrinic derivatives disclosed in U.S. Pat. No. 5,972,247.

EXAMPLES

The present invention will be explained in more detail with reference to Examples hereinafter.

A representative synthetic route for preparing compounds of formula [I] is shown in Scheme 1 and is described in full in Examples 1 to 4 which follow:

Scheme 1

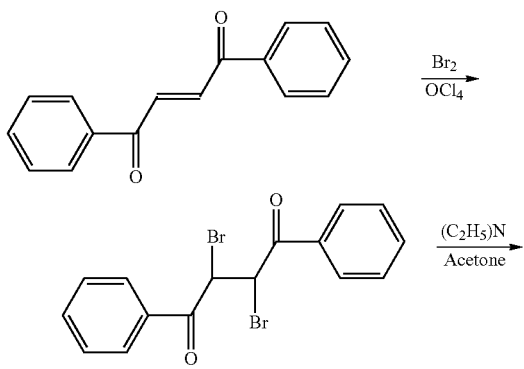

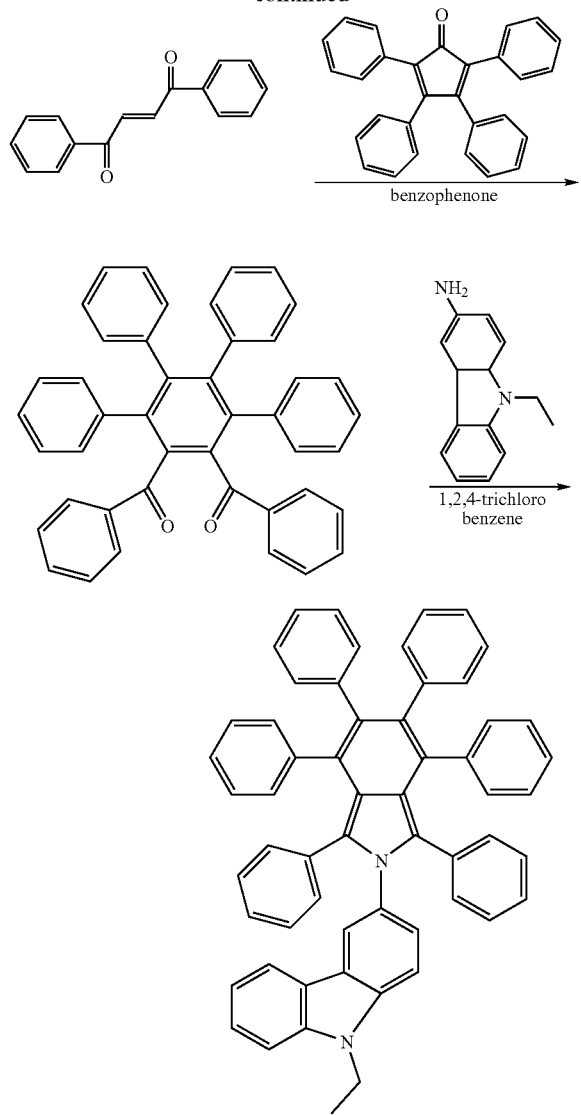

This general scheme can be varied by the person skilled in the art in order to produce other compounds of formula [I]. For example, diamines could be used in the final step, instead of amines, in order to synthesise compounds of formula [IV] or formula [V]. Exemplary schemes for preparing compounds of formula [IV] and formula [V] are given in Examples 5 and 6 which follow.

Example 1

Synthesis of 1,2-bis(benzoyl)-1,2-dibromoethylene{1,2-bis(benzolyl-1,2-dibromoethane}

1,2-bisbenzoyl-ethylene ($C_{16}H_{12}O_2$: 236.27, 5.5 g, 23.3 mmol) was dissolved in 40 ml $CHCl_3$, to which was added a solution of bromine (FW: 159.81, d=3.1023, 1.2 ml, 23.3 mmol) in $CHCl_3$ (8 ml). The reaction mixture was stirred under an atmosphere of nitrogen for 30 min and concentrated under reduced pressure to give a white solid. After recrystallization from ether/EtAc, the yield was 7.2 g (78.4%).

Example 2

Synthesis of 1,2-bis(benzolyl)acetylene

To a solution of 1,2-bisbenzoyl-1,2-dibromoethylene ($C_{16}H_{12}O_2Br_2$: 396.08, 6 g, 15.15 mmol) in reagent-grade acetone (150 ml) under an atmosphere of nitrogen was added triethylamine ($C_6H_{15}N$, 101.19, d=0.72, 4.4 ml, 30.30 mmol). After stirring the reaction mixture for 10 min at reflux temperature, the quaternary salt was filtered and the filtrate concentrated under reduced pressure. After recrystallization from ethanol, the yield was 3.02 g (yellow color, 85%).

Example 3

Synthesis of 1,2-bis(benzoyl)-3,4,5,6-tetraphenylbenzene 1,2-bis(benzoyl)acetylene ($C_{16}H_{10}O_2$, 234.27, 2 g, 8.54 mmol), tetraphenylcyclopenta-dienone ($C_{29}H_{20}O$, 384.47, 3.28 g, 8.54 mmol), and 40 g benzophenone were refluxed for 2 hr under an atmosphere of nitrogen. The reaction mixture was cooled to 30° C. and poured into a large volume (250 ml) of methanol. The tan precipitation was washed with methanol (2×10 ml) and refluxed in toluene (25 ml) charcoal (a spoon) to give a white crystal in 43% yield.

Example 4

Synthesis of 1,3,4,5,6,7-hexaphenyl-2-{3'-(9-ethyl-carbazolyl)}-isoindole (HPCzl).

A 50 ml three-necked flask equipped with a $N_2$ inlet, a condenser and a magnetic stirrer was charged with 1,2-bisbenzoyl-3,4,5,6-tetraphenylbenzene ($C_{44}H_{30}O_2$, 590.72, 1 g 1.69 mmol), 3-amino-9-ethylcarbazole (90%, $C_{14}H_{14}N_2$, 1.19 g, 5.08 mmol), 1,2,4-trichlorobenzene (15 ml, bp. 214° C.), and p-toluenesulfonic acid monohydrate (0.1 g, 0.51 mmol). The mixture was kept at 200° C. for 2 hr and then the resulting dark black solution was cooled down to room temperature, to which 50 ml of methanol was added. The solid precipitate was filtered and washed with 20 ml of methanol three more times. The yellow solid was then recrystallized from toluene twice to give 0.6 g of 1,3,4,5,6,7-hexaphenyl-2-{3'-(9-ethylcarbazolyl)}-isoindole (46.2% yield): mp 311.5° C.; $^1$H NMR (300 MHz, in $CDCl_3$) δ (ppm): 1.33 (t, 3H, —$CH_3$ 4.21 (q, 2H, —$CH_2$—), 6.54–7.60 (m, 36H), 7.79 (d, 1H); calculated for $C_{58}H_{42}N_2$: C: 90.82%, H: 5.47%, N: 3.65; found: C: 90.84, H: 5.43, N: 3.63%.

Example 5

Synthesis of 1,4-di(1",3",4",5",6",7"-hexaphenyl-2"-isoindolyl)-benzene (DH PIB)

A 50 ml three-neck flask equipped with a $N_2$ inlet, a condenser and a magnetic stirrer was charged with 1,2-bisbenzoyl-3,4,5,6-tetraphenylbenzene ($C_{44}H_{30}O_2$, 590.72, 1 g 1.69 mmol), 1,4-diaminebenzene ($C_6H_8H_2$, 108, 0.092 g, 0.85 mmol), 1,2,4-trichlorobenzene (10 ml, bp. 214° C.), and p-toluenesulfonic acid monohydrate (32.8 mg, 0.17 mmol). The mixture was kept at 200° C. for 24 hr and then the resulting dark black solution was cooled down to room temperature, to which 60 ml of methanol was added. The solid precipitate was filtered and washed with 30 ml of methanol three more times. The yellow solid was then recrystallized from toluene twice to give 0.31 g of 1,4-di (1",3",4",5",6",7"-hexaphenyl-2"-isoindolyl)-benzene: DHPIB, 28% yield, MS: m/z 1253.0 (M+20).

Example 6

Synthesis of 4,4'-di(1",3",4",5",6",7"-hexaphenyl-2"-isoindolyl)-biphenyl (DHPIBP):

A 50 ml three-neck flask equipped with a $N_2$ inlet, a condenser and a magnetic stirrer was charged with 1,2-bisbenzoyl-3,4,5,6-tetraphenylbenzene ($C_{44}H_{30}O_2$, 590.72, 1 g 1.69 mmol), benzidine (95%, $C_{12}H_{12}N_2$, 184.2, 0.165 g, 0.85 mmol), 1,2,4-trichlorobenzene (10 ml, bp. 214° C.), and p-toluenesulfonic acid monohydrate (32.8 mg, 0.17 mmol). The mixture was kept at 200° C. for 24 hr and then the resulting dark black solution was cooled down to room temperature, to which 50 ml of methanol was added. The solid precipitate was filtered and washed with 20 ml of methanol three more times. The yellow solid was then re-crystallized from toluene twice to give 0.22 g of 4,4'-di-(1",3",4",5",6",7"-hexaphenyl-2"-isoindolyl)-biphenyl: DHPIBP, 20% yield, MS: m/z 1330.0 (M+20).

Example 7

Properties of 1,3,4,5,6,7-hexaphenyl-2-{3'-(9-ethylcarbazolyl)}-isoindole (HPCzl)

Figure 3:
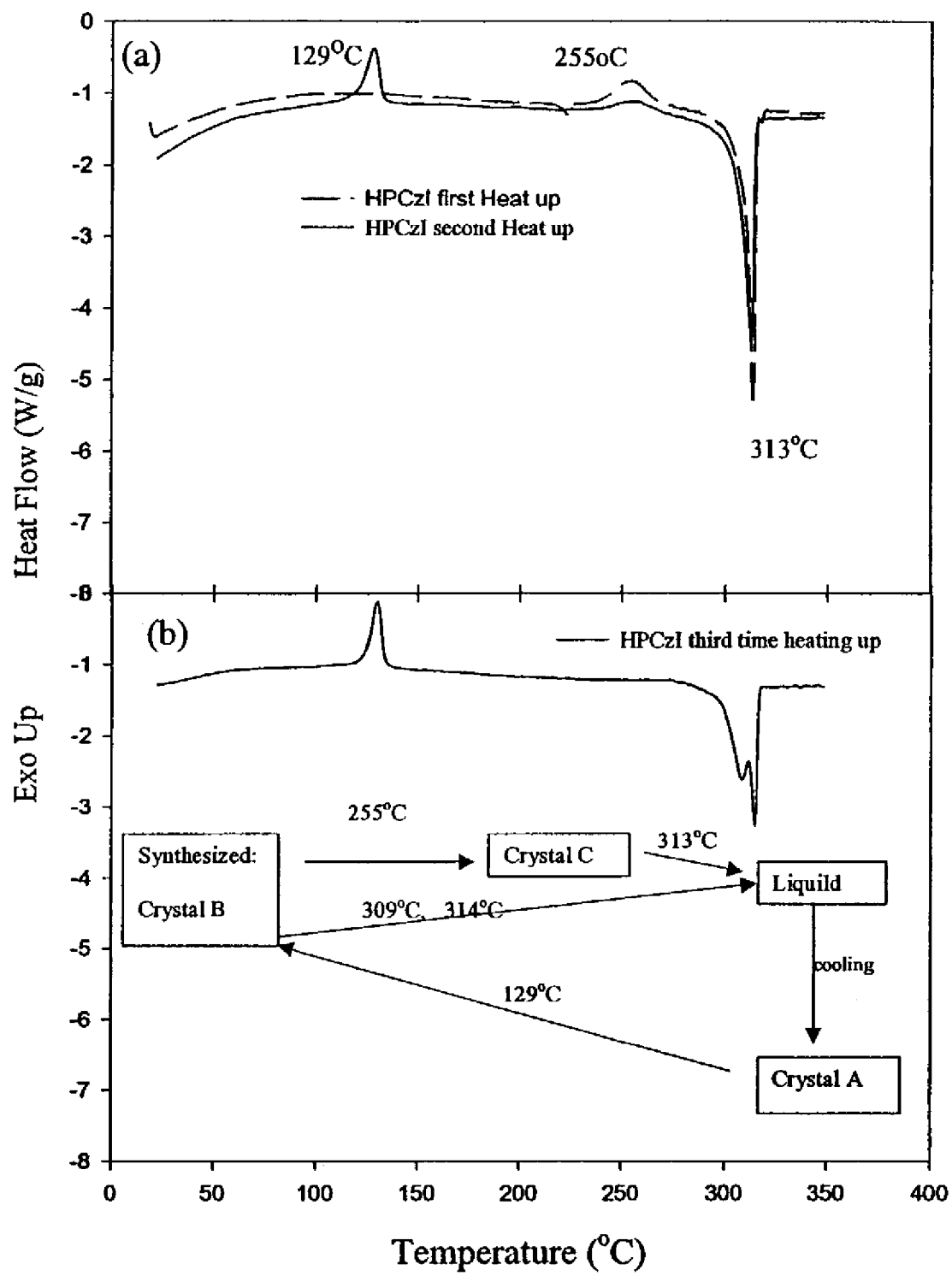
FIG. 3 shows the absorption and photoluminescence spectra from dilute solutions of HPCzl in different solvents and HPCzl film.

Thermal analysis using scanning calorimetry indicates that the compound has a high melting point of 311.5° C. (see FIG. 3). Its bulky structure leads to good film-forming properties via thermal evaporation. Aside from the high hole mobility, the compound also possesses other important attributes required for a good hole-transporting host material for applications in organic electroluminescence.

Figure 4:
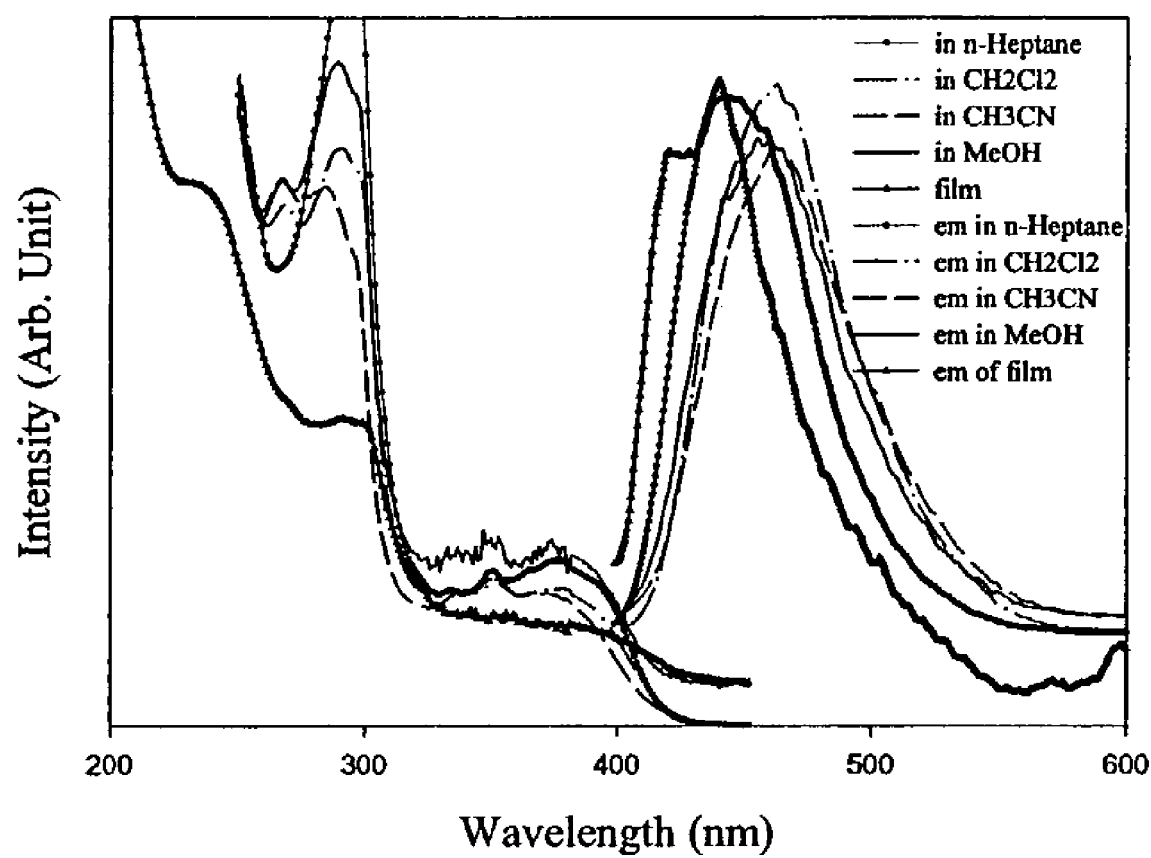
FIG. 4 shows the thermal analysis of HPCzl using differential scanning calorimetry.

Absorption and the photoluminescence spectra of HPCzl were measured in dilute solutions of different solvents as well as in the form of an HPCzl film deposited on a quartz substrate. The results are summarized in table 1, and the spectra are shown on FIG. 4. The absorption peaks of HPCzl in different solvents are almost the same, with peaks at 350–370 and 290 nm. This suggests that the polarity of solvent has little influence on the energy levels of HPCzl ground state molecules. However, the emission peaks of HPCzl in different solvents show clear differences. The emission of HPCzl peaks at 444 nm in n-Heptane (nonpolar), 455 nm in MeOH (a polar proton solvent) and 462 nm in $CH_2Cl_2$ (medium polarity) and $CH_3CN$ (a strongly polar aproton solvent). The fluorescence quantum yields of HPCzl in different solvents were also obtained using quinine sulfate in 1M sulphuric acid as the standard (fluorescence quantum yield of 0.546). The fluorescence quantum yields in aproton solvents have values ranging from 0.31 to 0.37 whereas the fluorescence quantum yield in aproton solvent (methanol) is 0.63.

TABLE 1

Spectra and photophysical data of compound HPCzl in different solvents

| Solvents | UV-Vis Absorption λmax/nm (ϵ/$M^{-1}cm^{-1}$) | Photo Emission $\lambda_{em}$ (nm) | FWHM (nm) | $\Phi_{pl}^a$ (%) |
|---|---|---|---|---|
| n-Heptane | 379 (15960), 351 (14880), 292 (71710) | 444.4 | 61 | 0.31 |
| $CH_2Cl_2$ | 374 (13290), 352 (14090), 291 (55330) | 462.9 | 64 | 0.37 |
| $CH_3CN$ | 372 (12800), 351 (14170), 284 (51660) | 461.6 | 64 | 0.31 |
| $MeOH^a$ | 374, 347, 289 | 455.2 | 64 | 0.63 |
| Thin Film[b] | 340–380, 300, 240 | 440.0 | 55 | — |

[a] For HPCzl in MeOH, due to the insolubility, the values of ordinate for absorption were too small (less than 0.03) to be used for accurate ϵ ($M^{-1}cm^{-1}$) calculation.
[b] HPCzl thin film with thickness of 80 Å on quartz substrate by vacuum deposition.
The extinction coefficients ϵ ($M^{-1}cm^{-1}$) and the Photo luminescence quantum yield $\Phi_{pl}$ for HPCzl film are unavailable.

Example 8

Method for Fabrication of Electroluminescence Device

Devices were fabricated with a configuration of glass/indium-tin-oxide (ITO: 30 Ω/)/hole-transporting materials (800 Å)/AIQ$_3$ (600 Å)/Mg:Ag (2000 Å; mass ratio of Mg to Ag is 10:1) according to the following procedure. The ITO glass substrate was cleaned with detergent and deionized water, and dried in an oven for about two hours. It was then treated with UV-Ozone for 25 minutes before loading into a deposition chamber with a base pressure of $5\times10^{-7}$ Pa. The organic films and metal electrode were sequentially deposited on the substrate by thermal evaporation. The deposition rates were 2–3 Å/s for the organic materials and 5–7 Å/s for the cathode metals. The current-voltage-luminance characteristics and EL spectra were measured with a computer-controlled direct-current power supply and a Spectrascan PR650 photometer at room temperature. The emission area of the devices is 0.1 $cm^2$, as defined by the overlapping area of the anode and cathode.

Example 9

Figure 5:
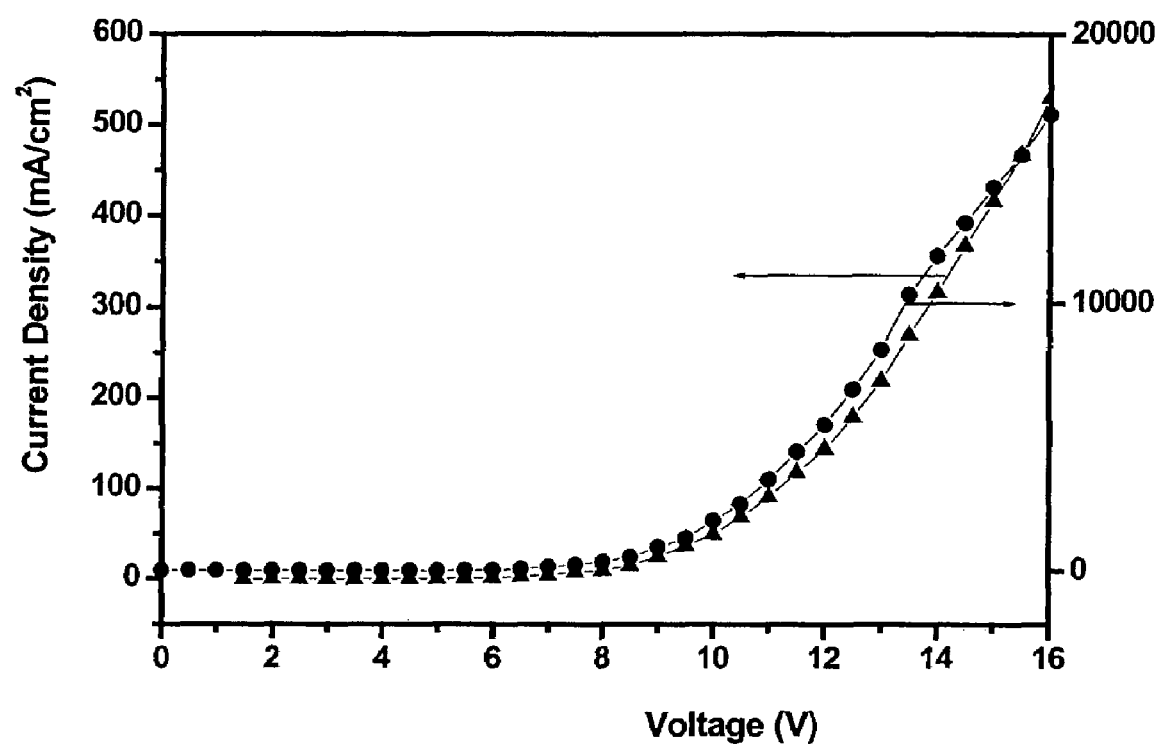
FIG. 5 shows the performance of a device constructed in accordance with the invention.

An electroluminescence device with 1,3,4,5,6,7-hexaphenyl-2-{3'-(9-ethylcarbazolyl)}-isoindole (HPCzl) as hole-transporting layer was fabricated by following the same general procedure as Example 8. The performance as a hole-transporting material in a double layer electroluminescent device was investigated, and the results are shown in FIG. 5. At a drive voltage of 8.8 V and a current density of 20 mA/$cm^2$, the device with a configuration of ITO (30 Ω/)/HPCzl (80 nm)/AIQ$_3$ (60 nm)/MgAg (10:1, 200 nm) showed a green AIQ$_3$ emission with a current efficiency of 3.5 cd/A.

The results of the foregoing specific examples of the present invention demonstrate that the new compounds of formula [I] have good hole-transporting properties and high thermal stability. The electroluminescent devices with the compounds disclosed in the present invention as hole-transporting materials showed good light emitting efficiencies.

The foregoing is offered primarily for the purposes of illustration. It will be readily apparent to those skilled in the art that numerous variations, modifications and substitutions may be made in the materials, procedural steps and conditions described herein without departing from the spirit and scope of the invention.

The invention claimed is:
1. A compound of formula [I]:

X—R  [I]

wherein X represents the group:

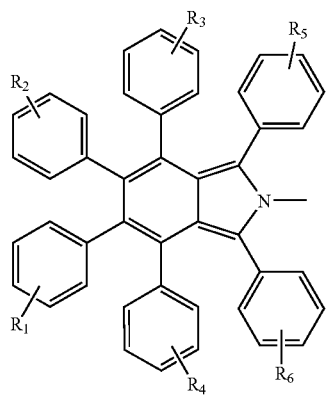

and R is either (i) represented by the formula [II]

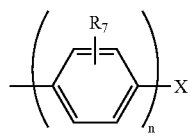  [II]

wherein n is 1 or 2, and the or each $R_7$ group is independently selected from the group consisting of hydrogen and halogen atoms, cyano, nitro, mercapto, carbonyl and sulfone groups, and optionally substituted alkyl, haloalkyl, hydroxyalkyl, aryl, alkoxy, aryloxy, alkylamino, arylamino, alkylthio, arylthio, ester, siloxy, cyclic hydrocarbon and heterocyclic groups;

or (ii) is selected from the group consisting of optionally substituted alkyl, hydroxyalkyl, aryl, cyclic hydrocarbon and heterocyclic groups;

wherein in each case $R_1$–$R_6$ are each independently selected from the group consisting of hydrogen and halogen atoms, cyano, nitro, mercapto, carbonyl and sulfone groups, and optionally substituted alkyl, haloalkyl, hydroxyalkyl, aryl, alkoxy, aryloxy, alkylamino, arylamino, alkylthio, arylthio, ester, siloxy, cyclic hydrocarbon and heterocyclic groups; except when R is aryl, then one of $R_5$ and $R_6$ is other than hydrogen; and except when R is methyl, then one of $R_5$ and $R_6$ is other than fluorine, other than phenoxy, and other than hydrogen; and except when R is phenyl, then one of $R_5$ and $R_6$ is other than chlorine; and except when R is tolyl, then one of $R_5$ and $R_6$ is other than phenoxy, and other than fluorine; and when R is tolyl, then one of $R_5$ and $R_6$ is other than fluorine and the other of $R_5$ and $R_6$ is other than arylamino.

2. The compound of claim 1 wherein R is selected from the group consisting of alkyl, haloalkyl, aryl and heterocyclic groups.

3. The compound of claim 1 having formula [IV]:

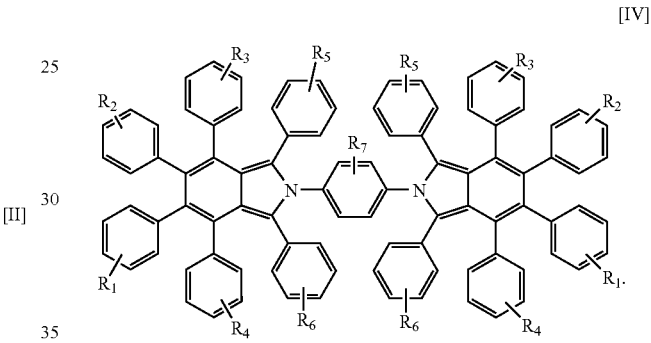  [IV]

4. The compound of claim 3 wherein the or each $R_7$ group is independently selected from the group consisting of alkyl, haloalkyl, aryl and heterocyclic groups.

5. The compound of claim 1 having the formula [V]:

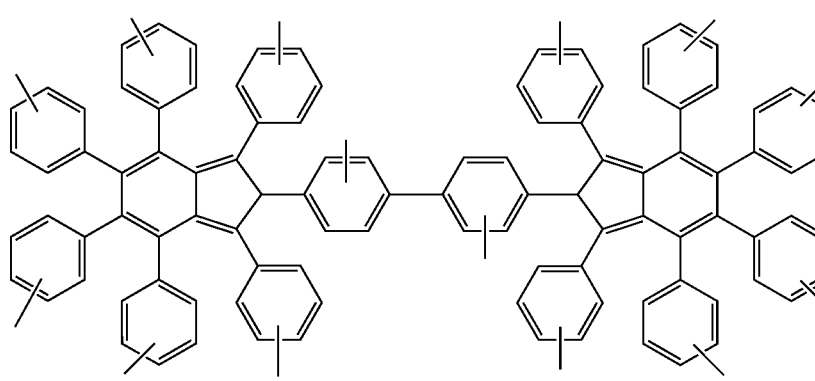  [V]

6. The compound of claim 5 wherein the or each $R_7$ group is independently selected from the group consisting of alkyl, haloalkyl, aryl and heterocyclic groups.

7. The compound of claim 1 wherein $R_1$–$R_6$ are selected from the group consisting of alkyl, haloalkyl, aryl and heterocyclic groups.

8. The compound of claim 1 wherein $R_1$–$R_6$ are hydrogen atoms when R is other than aryl and other than methyl.

9. An organic electroluminescence device comprising
an anode;
a cathode;
a hole transporting layer; and
an electron transporting layer;
wherein the hole-transporting layer is disposed between the anode and the electron-transporting layer and the electron-transporting layer is disposed between the cathode and the hole-transporting layer, and the hole-transporting layer comprises a compound of formula [I]

$$X\text{—}R \qquad [I]$$

wherein X represents the group:

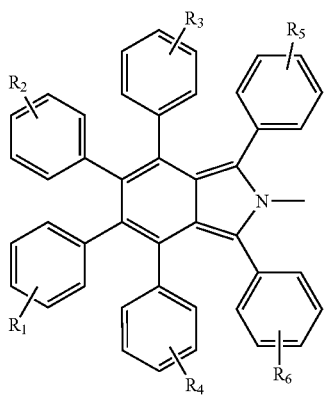

and R is either (i) represented by the formula [II]

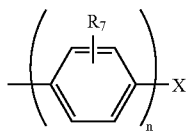

[II]

wherein n is 1 or 2, and the or each $R_7$ group is independently selected from the group consisting of hydrogen and halogen atoms, cyano, nitro, mercapto, carbonyl and sulfone groups, and optionally substituted alkyl, haloalkyl, hydroxyalkyl, aryl, alkoxy, aryloxy, alkylamino, arylamino, alkylthio, arylthio, ester, siloxy, cyclic hydrocarbon and heterocyclic groups;

or (ii) is selected from the group consisting of optionally substituted alkyl, hydroxyalkyl, aryl, cyclic hydrocarbon and heterocyclic groups;

wherein in each case $R_1$–$R_6$ are each independently selected from the group consisting of hydrogen and halogen atoms, cyano, nitro, mercapto, carbonyl and sulfone groups, and optionally substituted alkyl, haloalkyl, hydroxyalkyl, aryl, alkoxy, aryloxy, alkylamino, arylamino, alkylthio, arylthio, ester, siloxy, cyclic hydrocarbon and heterocyclic groups; except when R is aryl, then one of $R_5$ and $R_6$ is other than hydrogen: and except when R is methyl, then one of $R_5$ and $R_6$ is other than fluorine, other than phenoxy, and other than hydrogen; and except when R is phenyl, then one of $R_5$ and $R_6$ is other than chlorine; and except when R is tolyl, then one of $R_5$ and $R_6$ is other than phenoxy, and other than fluorine; and when R is tolyl, then one of $R_5$ and $R_6$ is other than fluorine and the other of $R_5$ and $R_6$ is other than arylamino.

10. An organic electroluminescence device according to claim 9 wherein R is selected from the group consisting of alkyl, haloalkyl, aryl and heterocyclic groups.

11. An organic electroluminescence device according to claim 9 wherein the hole transporting layer comprises a compound of formula [IV]:

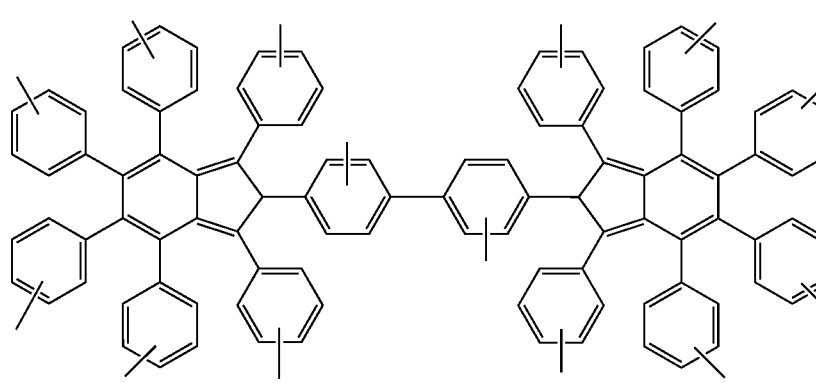

12. An organic electroluminescence device according to claim 9 wherein the or each $R_7$ group is independently selected from the group consisting of alkyl, haloalkyl, aryl and heterocyclic groups.

13. An organic electroluminescence device according to claim 9 wherein the hole-transporting layer comprises a compound of formula [V]:

14. An organic electroluminescence device according to claim 9 wherein the or each $R_7$ group is independently selected from the group consisting of alkyl, haloalkyl, aryl and heterocyclic groups.

15. An organic electroluminescence device according to claim 9 wherein $R_1$–$R_6$ are selected from the group consisting of alkyl, haloalkyl, aryl and heterocyclic groups.

16. An organic electroluminescence device according to claim 9 wherein $R_1$–$R_6$ are hydrogen atoms when R is other than aryl and other than methyl.

17. An organic electroluminescence device according to claim 9 wherein a luminescent material is incorporated in the electron transporting layer.

18. An organic electroluminescence device according to claim 9 wherein a luminescent material is incorporated in the hole transporting layer.

19. An organic electroluminescence device according to claim 9 wherein a luminescent layer is disposed between the electron transporting layer and the hole transporting layer.

20. An organic electroluminescence device according to claim 9 wherein the hole transporting layer comprises an additional hole transporting compound selected from the group consisting of optionally substituted phthalocyanine derivatives, napththalocyanine derivatives, porphyrin derivatives, pyrazoline derivatives, carbazole derivatives, thiophene derivatives, aromatic tertiary amine derivatives, benzidine derivatives, triphenylamine derivatives, polyvinylcarbazole and polysilane.

21. An organic electroluminescence device according to claim 20 wherein the additional hole transporting compound has a structure selected from the group consisting of:

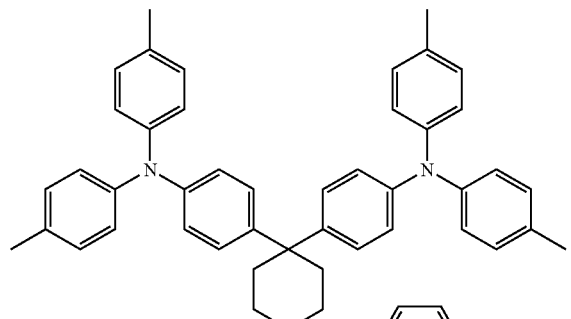

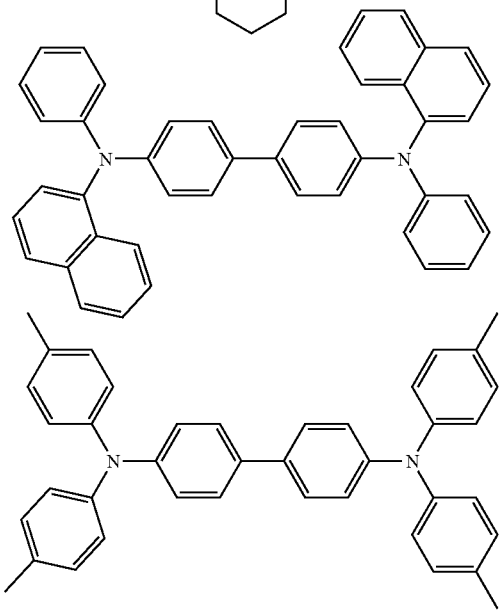

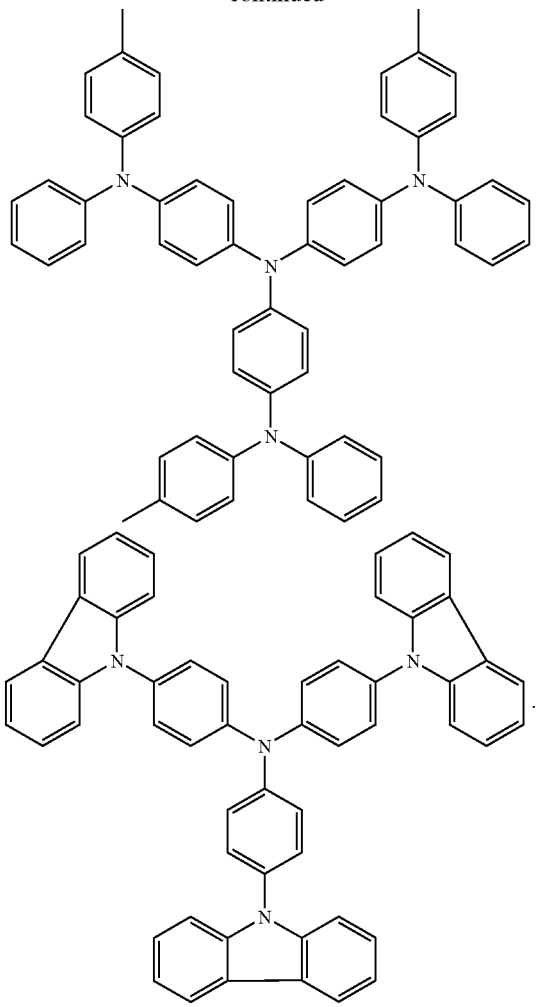

22. An organic electroluminescence device according to claim 9 additionally comprising a hole injection material disposed between the anode and the hole transporting layer.

23. A method of using a compound of formula [I] in an electroluminescence device:

X—R  [I]

wherein X represents the group:

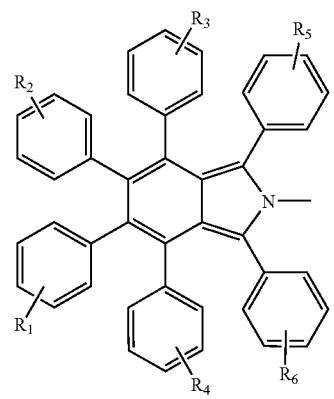

and R is either (i) represented by the formula [II]

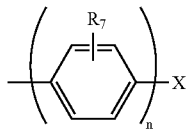

[II]

wherein n is 1 or 2, and the or each $R_7$ group is independently selected from the group consisting of hydrogen and halogen atoms, cyano, nitro, mercapto, carbonyl and sulfone groups, and optionally substituted alkyl, haloalkyl, hydroxyalkyl, aryl, alkoxy, aryloxy, alkylamino, arylamino, alkylthio, arylthio, ester, siloxy, cyclic hydrocarbon and heterocyclic groups;

or (ii) is selected from the group consisting of optionally substituted alkyl, hydroxyalkyl, aryl, cyclic hydrocarbon and heterocyclic groups;
wherein in each case $R_1$–$R_6$ are each independently selected from the group consisting of hydrogen and halogen atoms, cyano, nitro, mercapto, carbonyl and sulfone groups, and optionally substituted alkyl, haloalkyl, hydroxyalkyl, aryl, alkoxy, aryloxy, alkylamino, arylamino, alkylthio, arylthio, ester, siloxy, cyclic hydrocarbon and heterocyclic groups; except when R is aryl, then one of $R_5$ and $R_6$ is other than hydrogen; the method comprising providing a compound of formula [I], and incorporating said compound as a hole-transporting material within an electroluminescence device which further comprises an anode, a cathode and an electron-transporting material.

* * * * *